(12) United States Patent
Weir

(10) Patent No.: US 6,509,494 B1
(45) Date of Patent: Jan. 21, 2003

(54) LOW ODOR REACTIVE COALESCENT

(75) Inventor: William David Weir, Levittown, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/510,899

(22) Filed: Feb. 23, 2000

Related U.S. Application Data

(63) Continuation-in-part of application No. 09/133,144, filed on Aug. 12, 1998, now abandoned.
(60) Provisional application No. 60/057,283, filed on Aug. 29, 1997.

(51) Int. Cl.$^7$ .............................. C07C 69/52; C04B 9/02
(52) U.S. Cl. ................... 560/220; 560/224; 106/14.13
(58) Field of Search ............................... 560/220, 224; 106/14.13

(56) References Cited

U.S. PATENT DOCUMENTS

| | | |
|---|---|---|
| 4,097,677 A | 6/1978 | Emmons et al. |
| 4,141,868 A | 2/1979 | Emmons et al. |
| 5,072,027 A | 12/1991 | Kobayashi et al. |

OTHER PUBLICATIONS

Chem. Abstr. 128: 49239 (JP09302053), 1997.*
Research Disclosure, Feb. 1998/113, # 40610.

* cited by examiner

*Primary Examiner*—Paul J. Killos
(74) *Attorney, Agent, or Firm*—Alan Holler

(57) ABSTRACT

A process is provided for preparing a low odor composition containing a dicyclopentenyl ester including the steps of preparing a distillation mixture containing the dicyclopentenyl ester and from 10 to 10,000 parts per million by weight based on weight of the dicyclopentenyl ester, of a suitable inhibitor; distilling the distillation mixture at a temperature in the range of 140° C. to 250° C.; collecting a first distillation fraction of the dicyclopentenyl ester; and then collecting a second distillation of the dicyclopentenyl ester; wherein the level of dicyclopentenyloxy(meth)acrylate in the second distillation fraction is in the range of 0 to 0.2 weight %, based on the weight of the dicyclopentenyl ester in the second distillation fraction. The second distillation fraction provides a low odor composition of the dicyclopentenyl ester which is useful as a reactive coalescent.

12 Claims, No Drawings

LOW ODOR REACTIVE COALESCENT

This application is a continuation in part of application Ser. No. 09/133,144 filed Aug. 12, 1998 abandoned which is based on provisional application Ser. No. 60/057,283 filed Aug. 29, 1997, abandoned.

This invention relates to compositions which are useful as reactive coalescents. In particular, the invention relates to compositions which are useful as reactive coalescents which are substantially free from odor, their method of preparation, and their use in aqueous coating compositions.

Water based polymers are used extensively in coating compositions. Many applications, such as gloss paint and semigloss paint formulations, require the properties of a hard polymer, i.e. a polymer with a glass transition temperature significantly above the ambient temperature. For the hard polymer to form a film at ambient temperature, the hard polymer is typically formulated with volatile coalescent. The volatile coalescent swells the hard polymer and lowers the glass transition of the hard polymer to allow film formation. After formation of the film, the volatile coalescent evaporates, leaving a hard polymer film. The use of volatile solvents including volatile coalescents, is coming under increased scrutiny as they are a source of volatile organic compounds (VOC's) which can contribute to atmospheric pollution. Recent legislation is mandating the use of coating compositions with lower levels of VOC including VOC free coatings. Further, volatile coalescents are sources of residual odors which may be bothersome, particularly in enclosed environments.

Attempts have been made to use "reactive coalescents" to replace volatile coalescents. Reactive coalescents are compounds which aid in film formation in a similar manner as conventional coalescents but have low volatility and react to become part of the final coating.

One class of reactive coalescents is vinyl reactive coalescents such as dicyclopentenyl esters which include dicyclopentenyloxymethacrylate (DCPOMA), also known as dicyclopentenyl methacrylate, dicyclopentenyloxyacrylate (DCPOA), also known as dicyclopentenyl acrylate, dicyclopentenyloxyethylmethacrylate (DCPOEMA), and dicyclopentyloxyethylacrylate (DCPOEA). These dicyclopentenyl esters have low volatility, and are believed to react through reaction of their vinyl groups to increase the hardness and toughness of coated films. However, DCPOMA and DCPOA, although having low volatility, have objectionable odors which limit their use as reactive coalescents in coating applications, particularly in applications which require baking at elevated temperatures. U.S. Pat. No. 4,141,868 to Emmons et al. teaches the use of DCPOEMA and DCPOEA as vinyl reactive coalescents for aqueous film-forming coating dispersions. Emmons discloses that in contrast to DCPOMA and DCPOA, compositions containing DCPOEMA and DCPOEA do not have an objectionable or even a detectable odor. However, the detection and perception of odor is known to be highly subjective. Further, the standards as to what constitutes a low or no odor composition have changed since the disclosure of Emmons. I have found that despite the disclosure of Emmons, DCPOEMA prepared by the method taught in Emmons still has levels of odor which are objectionable and limit the use of DCPOEMA as a reactive coalescent in coating compositions. There exists a need to provide vinyl reactive coalescents such as DCPOEMA and DCPOEA preparations with lower levels of odor or in particular, no discernible odor, to meet current low odor expectations for coating compositions. A current problem is that DCPOEMA and DCPOEA preparations produced by existing processes have detectable levels of odor that is objectionable to personnel who prepare the coating compositions and/or persons who use them under most conditions of preparation and use. Further, these odors from the DCPOEMA and DCPOEA preparations are more noticeable as modifications to coating compositions have been made to remove other odor causing components such as cosolvents or ammonia which may mask odoriferous smells from the DCPOEMA and DCPOEA preparations. The objectionable smell attributed to DCPOEMA and DCPOEA preparations has limited the use of these preparations in coating compositions.

I have discovered that the odor is not a property of the DCPOEMA, but rather the source of the objectionable odor in the DCPOEMA preparations which are produced by disclosed processes is trace levels of DCPOMA. The DCPOMA is a byproduct of the reactions to prepare DCPOEMA and is not removed by disclosed distillation processes. I have identified a distillation process which is adaptable to an industrial scale process that prepares DCPOEMA and DCPOEA which are substantially-free of DCPOMA and DCPOA and have no objectionable odor. These new preparations of DCPOEMA and DCPOEA are particularly useful as reactive coalescents for aqueous film-forming dispersions.

The distillation process of this invention involves the collection of a first distillation fraction which is rich in the DCPOMA and DCPOA impurities followed by the collection of a second distillation fraction containing DCPOEMA and DCPOEA which is substantially-free of DCPOMA and DCPOA. Since the DCPOMA and DCPOA are distilled into the first distillation fraction, distillation processes without fractional collection of the distillate are not capable of decreasing the concentrations of DCPOMA and DCPOA in DCPOEMA and DCPOEA. Rather, distillation processes without fractional collection of the distillate may be increasing the concentrations of DCPOMA and DCPOA in the distilled DCPOEMA and DCPOEA compared to the concentrations in the distillation mixture, as a fraction of DCPOEMA and DCPOEA often remains undistilled.

In the first aspect of this invention, a composition is provided including at least one dicyclopentenyl ester selected from the group of dicyclopentenyl esters having formula I:

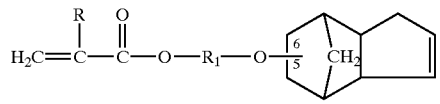

where R represents a H or methyl group and $R_1$ represents a $C_2$–$C_{12}$ alkylene group or a $C_2$–$C_{12}$ oxyalkylene group containing one or more oxygen atoms joining alkylene segments of the groups, each such segment having a chain length of at least two carbon atoms extending between the oxygen atoms and a level of dicyclopentenyloxy(meth)acrylate in the range of from 0 to 0.2 weight % based on the weight of the at least one dicyclopentenyl ester.

In the second aspect of this invention, a process for preparing a low odor composition of a dicyclopentenyl ester selected from the group of dicyclopentenyl esters having formula I:

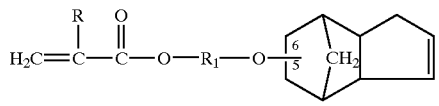

wherein R represents a H or methyl group and $R_1$ represents a $C_2$–$C_{12}$ alkylene group or a $C_2$–$C_{12}$ oxyalkylene group containing one or more oxygen atoms joining alkylene segments of the groups, each such segment having a chain length of at least two carbon atoms extending between the oxygen atoms, including the steps of preparing a distillation mixture containing the dicyclopentenyl ester and from 10 to 10,000 parts per million by weight based on weight of the dicyclopentenyl ester, of at least one inhibitor selected from the group consisting of phenothiazine, 4-hydroxy-2,2,6,6-tetramethyl piperidinyloxy free radical, 4-methacryloyloxy-2,2,6,6-tetramethyl piperidinyloxy free radical, 4-hydroxy-2,2,6,6-tetramethyl N-hydroxy piperidine, cupric acetate, cupric chloride, 2,6-dichlorobenzoquinone, 2-nitrophenol, p-phenylenediamine, and 1,4-naphthoquinone; distilling the distillation mixture at a temperature in the range of 140° C. to 250° C.; collecting at least one first distillation fraction containing from 2 to 30 weight % of the dicyclopentenyl ester, based on the weight of the dicyclopentenyl ester in the distillation mixture; and collecting at least one second distillation fraction containing from 98 to 70 weight % of the dicyclopentenyl ester, based on the weight of the dicyclopentenyl ester in the distillation mixture; wherein the level of dicyclopentenyloxy(meth)acrylate in the second distillation fraction is in the range of 0 to 0.2 weight %, based on the weight of the dicyclopentenyl ester in the second distillation fraction, wherein the second distillation fraction is the low odor composition of the dicyclopentenyl ester.

In the third aspect of this invention, a composition is provided including at least one compound selected from the group of compounds having formula I:

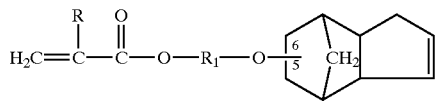

wherein R represents a H or methyl group and $R_1$ represents a $C_2$–$C_{12}$ alkylene group or a $C_2$–$C_{12}$ oxyalkylene group containing one or more oxygen atoms joining alkylene segments of the groups, each such segment having a chain length of at least two carbon atoms extending between the oxygen atoms wherein the improvement is the composition having a level of dicyclopentenyloxy(meth)acrylate in the range of 0 to 0.2%, based on the weight of the compounds of formula I.

As used herein, the term "(meth)acrylate" denotes both "acrylate" and "methacrylate", the term "(meth)acrylic" denotes both "acrylic" and "methacrylic", and the term "(meth)acryloyl" denotes both "acryloyl" and "methacryloyl". As used herein, the term "DCPO(M)A" denotes both DCPOMA and DCPOA, and the term "DCPOE(M)A" denotes both DCPOEMA and DCPOEA.

The reactive coalescents of the present invention are dicyclopentenyl alcohol esters of (meth)acrylic acids and are represented by formula I:

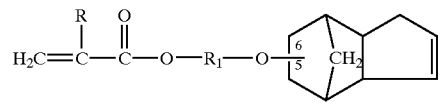

wherein R represents a H or methyl group and $R_1$ represents a $C_2$–$C_{12}$ alkylene group or a $C_2$–$C_{12}$ oxyalkylene group containing one or more oxygen atoms joining alkylene segments of the groups, each such segment having a chain length of at least two carbon atoms extending between the oxygen atoms. The ester-ether chain may be connected to either the 5-position or 6-position of the ring nucleus as indicated in formula I. The dicyclopentenyl alcohol esters of (meth)acrylic acid, also referred to herein as dicyclopentenyl esters, may comprise a mixture of the two isomers in which part of the ester-ether chain is substituted in the 5-position and part is in the 6-position.

Although not wanting to be limited to a single explanation for the source of odor in DCPOE(M)A preparations, I have discovered that trace levels of DCPO(M)A are detectable as an objectionable odor in compositions including DCPOE(M)A. One source of DCPO(M)A is from the esterification of dicyclopentenyl alcohol impurities in the ethylene glycol monodicyclopentenyl ether precursor used in the preparation of DCPOE(M)A. The dicyclopentenyl alcohol is produced as a byproduct from the reaction of dicyclopentadiene with excess ethylene glycol in the presence of an acid catalyst to produce the ethylene glycol monodicyclopentenyl ether precursor. In this reaction, the dicyclopentenyl alcohol is formed from the reaction of dicyclopentadiene with trace amounts of water, introduced with the excess diol and the acid catalyst, or from residual moisture in the reactor.

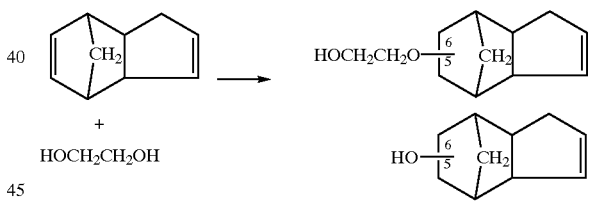

The ethylene glycol monodicyclopentenyl ether produced in this reaction step is typically isolated by distillation to remove catalyst and unreacted diol. However the distillation process does not completely remove the dicyclopentenyl alcohol impurity. The DCPOE(M)A is produced by the esterification of the ethylene glycol monodicyclopentenyl ether with (meth)acrylic acid or transesterified with an ester of (meth)acrylic acid in the presence an acid catalyst. In this step, the dicyclopentenyl alcohol impurity is also esterified to produce the DCPO(M)A.

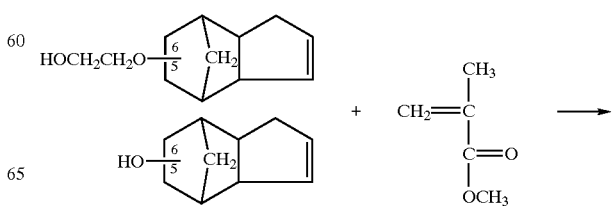

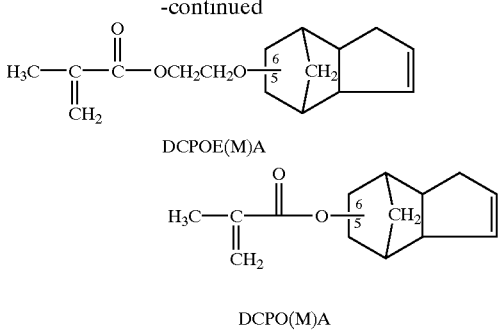

DCPOE(M)A

DCPO(M)A

The DCPOE(M)A may be purified by distillation to remove the DCPOE(M)A from the transesterification catalyst, reaction byproducts, and unreacted (meth)acrylic acid or (meth) acrylic ester. I have found that the DCPO(M)A impurities also can be readily removed from the DCPOE(M)A in a new distillation process which is adaptable to the large scale production of DCPOE(M)A. In contrast to earlier preparations of DCPOE(M)A, this distillation process involves the proper choice of inhibitor to prevent the polymerization of the DCPOE(M)A during distillation, the proper choice of distillation temperature, and the collection of a separate distillate fraction of DCPOE(M)A which is substantially free of DCPOMA and has no objectionable odor.

The reactive coalescents of formula I may be prepared by esterification reactions and transesterification reactions. Esterification reactions include the reactions of hydroxy-$R_1$-O-dicyclopentene with (meth)acrylic acid while transesterification reactions include reactions of hydroxy-$R_1$-O-dicyclopentene with esters of (meth)acrylic acid. A preferred synthesis is a transesterification reaction of hydroxy-$R_1$-O-dicyclopentene with an ester of (meth)acrylic acid. A more preferred synthesis is the transesterification reaction with a methyl ester of (meth)acrylic acid. Transesterification processes to produce dicyclopentenyl esters of (meth)acrylic acid are well known in the art and are taught in U.S. Pat. No. 4,097,677 to Emmons et al. and U.S. Pat. No. 4,141,868 to Kobayashi et al.

The composition of the this invention may be prepared by a fractional distillation process to remove the DCPO(M)A and other impurities from the dicyclopentenyl ester. The distillation process to purify the dicyclopentenyl ester requires the presence of an inhibitor in the distillation mixture to prevent polymerization of the dicyclopentenyl ester. The inhibitors suitable for this distillation process are characterized by their low volatility at the temperatures and pressures used in the distillation process which allows a significant fraction of the inhibitor to remain in the undistilled DCPOE(M)A during the distillation process. Further, the inhibitors may be anaerobic polymerization inhibitors. Suitable inhibitors include at least one inhibitor selected from phenothiazine, 4-hydroxy-2,2,6,6-tetramethyl piperidinyloxy free radical, 4-methacryloyloxy-2,2,6,6-tetramethyl piperidinyloxy free radical, and 4-hydroxy-2,2,6,6-tetramethyl N-hydroxy piperidine, cupric acetate, cupric chloride, 2,6 dichlorobenzoquinone, 2-nitrophenol, p-phenylenediamine, 1,4-naphthoquinone, and mixtures thereof. The amount of inhibitor added to the distillation mixture is typically from 10 to 10,000 parts per million based on the weight of dicyclopentenyl ester in the distillation mixture, and more preferably from 200 to 3,000 parts per million.

In the distillation process to prepare the composition of this invention, the first distillate or first cut of dicyclopentenyl ester contains a high level of DCPO(M)A and is isolated from the subsequent second distillate or second cut of the dicyclopentenyl ester which is substantially-free of DCPO(M)A and provides the composition of this invention. The first cut is the quantity of dicyclopentenyl ester which is distilled from the beginning of the distillation process to prior to the second cut. The second cut is the quantity of reactive coalescent distilled after the first cut to the completion of the distillation process. The first cut may contain from 2 to 30 weight % of the dicyclopentenyl ester, preferably from 5 to 20 weight % of the dicyclopentenyl ester, and most preferably from 7 to 16 weight % of the dicyclopentenyl ester, based on the weight of dicyclopentenyl ester in the distillation mixture. The first cut may be collected into a single container; for example, 10 weight % of the dicyclopentenyl ester is collected into a single container. Alternatively, the first cut may be subdivided into two or more fractions collected into separate containers; for example, 10 weight % of the dicyclopentenyl ester is collected into three containers wherein the first, second, and third containers hold 2 weight %, 5 weight %, and 3 weight % of the dicyclopentenyl ester in the distillation mixture, respectively. The second cut may contain from 40 to 98 weight % of the dicyclopentenyl ester, preferably form 50 to 95 weight % of the dicyclopentenyl ester, and most preferably from 60 to 93 weight % of the dicyclopentenyl ester, based on the weight of the dicyclopentenyl ester in the distillation mixture. The second cut may be collected into a single container or may be collected into two or more containers. As undistilled dicyclopentenyl ester may remain in the distillation apparatus after the completion of the distillation process, the total amount of the dicyclopentenyl ester contained in the first cut, the second cut, and optionally, any subsequent cuts, may not equal 100% of the dicyclopentenyl ester charged to the distillation vessel. The dicyclopentenyl ester which is substantially-free of DCPO(M)A has levels of DCPO(M)A in the range of 0 to 0.2 weight %, preferably in the range of 0 to 0.1 weight %, and more preferably in the range of 0 to 0.05 weight %, based on the weight of dicyclopentenyl ester. The level of DCPO(M)A may be determined by gas chromatography or other conventional analytical methods known in the art.

The distillation process of this invention may be performed as a purification and/or isolation step as part of a series of steps involving the synthesis, isolation, and purification of the dicyclopentenyl ester. For example, in the synthesis of DCPOEMA by the transesterification of ethylene glycol monodicyclopentenyl ether with methyl methacrylate, the crude DCPOEMA may be distilled by the distillation process of this invention to obtain DCPOEMA substantially free from DCPOMA. In another embodiment, the distillation process of this invention may be performed to purify an existing sample of dicyclopentenyl ester, such as a distillation to purify a sample of DCPOEMA which contains DCPOMA.

Various apparatus may be used for distilling the impure dicyclopentenyl ester to produce the composition of this invention. Suitable distilling columns include straight lead columns, Vigreux distilling columns, and Oldershaw distilling columns. Also suitable are distilling columns packed with materials which are non-reactive to the components contained within the distillation mixture such as porcelain, glass, steel wool, and fluorinated plastics.

The distillation process is conducted at a temperature in the range of 140° C. to 250° C., preferably in the range of 150° C. to 200° C., and more preferably in the range of 160° C. to 190° C., wherein the temperature is defined as the temperature of the distillation mixture in the distillation vessel. Although the distillation process may be conducted at a range of pressures, the use of lower pressures provides for a faster and lower temperature distillation process. Pressures in the range of 10 to 3000 pascals are preferred. A more preferred pressure range is 10 to 675 pascals.

In one embodiment, the composition of this invention may also be prepared by a distillation process using a thin film or wiped film still. In this process, the distillation mixture containing the undistilled dicyclopentenyl ester and the inhibitor is passed through a wiped film still to remove the DCPO(M)A. The material distilled from the wiped film still is the first distillation fraction and includes the DCPO(M)A and a portion of the dicyclopentenyl ester. The portion of the distillation mixture which passes through the still undistilled is collected to give the second distillation fraction of dicyclopentenyl esters of formula I which is substantially-free of DCPO(M)A and provides the composition of this invention. Alternately, the distillation mixture may be passed through the wiped film still more than one time to remove the DCPO(M)A and prepare the composition of this invention. The total material distilled from each pass through the wiped film still is the first distillation fraction. The process may be run continuously or semicontinuously with more than one pass through a single wiped film still, multiple passes through a single wiped film still, a single or multiple passes through more than one wiped film still.

The composition of this invention including the reactive coalescents of formula I may be stabilized to prevent polymerization during storage or handling by the addition of one or more polymerization inhibitors. Suitable polymerization inhibitors include hydroquinone, 4-methoxyphenol, phenothiazine, 4-hydroxy-2,2,6,6-tetramethyl-1-piperidinyloxy, and 4-oxo-tetramethyl-1-piperidinyloxy, and di-tertiary butyl nitroxyl. The polymerization inhibitors are typically used at levels of from 1 ppm to 10,000 ppm on a weight inhibitor to total weight of the composition basis. Preferred are inhibitor levels of from 50 ppm to 1,000 ppm. More preferred are inhibitor levels of from 100 ppm to 700 ppm.

The composition of this invention including the dicyclopentenyl esters of formula I may be admixed into formulations or polymerized with other ethylenically unsaturated monomers. Formulations such as coating compositions may contain polymeric binders including solution polymers and emulsion polymers as the main film-forming component. Suitable emulsion polymers include, for examples, emulsions of acrylic polymers, polyvinyl acetate and copolymers such as styrene/butadiene, vinyl acetate/acrylates, vinyl acetate/ethylene, styrene acrylics, vinyl acetate/versatate, and chlorinated copolymers.

The coating compositions may be nonaqueous or aqueous coating formulations. Aqueous coating compositions may include water and water miscible solvents such as glycols and glycol ethers, such as propylene glycol, ethylene glycol, ethylene glycol monomethyl ether, and the like. Alternately, the dicyclopentenyl esters of this invention are suitable for use in solvent based coating compositions. In a preferred embodiment, the coating composition is an aqueous coating composition. In a more preferred embodiment, the coating composition is an aqueous coating composition substantially-free of solvents and non-reactive coalescents.

In coating compositions, the composition of this invention including the dicyclopentenyl esters of formula I may be used to replace either partially or completely non-reactive coalescents such as volatile coalescents and plasticizers typically used in coating compositions. In one embodiment, the reactive coalescents of formula I are admixed with polymeric binder and optionally, pigments to prepare coating compositions. The level dicyclopentenyl ester that is used in a coating composition may be from 1% to 200% by weight, preferably 5% to 150%, based on the weight of the polymeric binder.

The coating composition may optionally include one or more driers to accelerate the cure of the dicyclopentenyl esters. Suitable driers include any polyvalent metal-containing complex or salt that catalyzes the oxidative curing of drying oils or drying oil-modified alkyd resins. Examples of the driers are various polyvalent metal salts including calcium, copper, zinc, manganese, lead, cobalt, iron, and zirconium as the cation. Simple inorganic salts are useful such as the halide, chloride, nitrate, sulfate. Salts of organic acids such as the acetylacetonate, acetate, propionate, and butyrate are useful. The driers may also be complex reaction products of metal oxides, acetates, or borates, naphthenic acids, or of $C_8$ to $C_{30}$ aliphatic acids. The driers disclosed in "Encyclopedia of Chemical Technology," Kirk-Othmer, Fourth Edition, Volume 8, pages 432–445, published by Interscience Encyclopedia, Inc., N.Y. (1993) may be useful. The proportion of the drier may be quite low and it is generally used in the amount of 0.0005 to 2% metal content by weight of the dicyclopentenyl ester of formula I in the coating composition.

Other additives to the coating composition include surfactants, rheology modifiers, extenders, wetting agents, dispersants, plasticizers, leveling agents, sequestering agents, defoaming agents, humectants, and biocides including mildewcides, fungicides, and bactericides. Suitable pigments include both organic and inorganic pigments such as titanium dioxide, calcium carbonate, clay, zinc oxide, molybdate orange, chrome yellow, and carbon black. The coating composition may also be colored with dyes.

EXAMPLE 1

Distillation of DCPOEMA to Prepare DCPOEMA Substantially Free of DCPOMA

A mixture of 212 grams of DCPOEMA (Aldrich Chemical Company) and 0.06 grams of 4-hydroxy-2,2,6,6-tetramethyl piperidinyloxy free radical was charged to the still pot. The mixture was heated and placed under vacuum. The distillation fractions were collected at approximately 133 pascals (1 mm of Hg). Table 1.1 has the distillation conditions and the analysis of the distillation fractions. The DCPOEMA and DCPOMA levels were characterized by gas chromatography (GC) and are reported as area % of the GC trace. The detection limit for the DCPOMA was less than 0.002%.

TABLE 1.1

| | Pot Temperature Range | Vapor Temperature Range | Weight of Sample | DCPOEMA | DCPOMA |
|---|---|---|---|---|---|
| DCPOEMA* (as supplied) | na | na | 212 grams | 96.0% | 0.95% |
| Cut 1 | 166–180° C. | 98.5–139.8° C. | 34 grams | 85.8% | 7.4% |
| Cut 2a | 176–180° C. | 134–139.8° C. | 68 grams | 96.0% | 0.2% |
| Cut 2b | 172–176° C. | 125.4–134.0° C. | 70 grams | 95.1% | 0.0% |
| Weighted Average of Cuts 2a and 2b | | | 138 grams | 95.5% | 0.1% |
| Weighted Average of Cuts 1, 2a, and 2b | | | 172 grams | 93.6% | 1.5% |

The first cut represented 14.3% of the DCPOEMA charged to the still pot. The second cut (2a+2b) represented 64.8% of the DCPOEMA charged to the still pot. The fractional distillation of the DCPOEMA gave a first cut which was rich in the DCPOMA impurity, compared to the unpurified DCPOEMA. The second cut was substantially free of DCPOMA. The distillation process of this invention produced DCPOEMA which was substantially free of DCPOMA and had no detectable odor. In comparison, distillation without fractional collection is represented by the weighted average of cuts 1, 2a, and 2b. Distillation without fractional collection of the distillate raised the DCPOMA level in the distilled DCPOEMA compared to the DCPOMA level in the undistilled sample.

EXAMPLE 2
Odor Evaluation of DCPOEMA

Samples of DCPOEMA were prepared with various levels of DCPOMA by blending fractionally distilled DCPOEMA with undistilled DCPOEMA. The odor levels of DCPOEMA samples were evaluated by a panel of eight people and rated according to the following scale:

1=no odor
2=faint odor
3=low odor
4=medium odor
5=strong odor

| Example | Rating | % DCPOMA |
|---|---|---|
| 2-1 | 1.00 | 0 |
| 2-2 | 1.71 | 0.025 |
| 2-3 | 2.46 | 0.1225 |
| 2-4 | 3.16 | 0.2200 |
| 2-5 | 3.42 | 0.3175 |
| 2-6 | 3.66 | 0.4150 |
| 2-7 | 4.12 | 0.6100 |
| 2-8 | 3.96 | 0.8050 |
| 2-9 | 4.25 | 1.00 |

The odor evaluation of examples 2-1 to 2-9 show that the odor decreased as the level of DCPOMA decreased in the DCPOEMA sample. Samples with levels of DCPOMA equal to or less than 0.2 wt %, based on DCPOEMA, were found by the odor panel to have low odor.

I claim:

1. A composition comprising at least one dicyclopentenyl ester selected from the group of dicyclopentenyl esters having formula I:

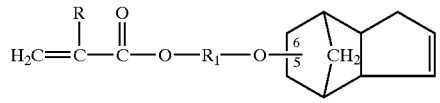

wherein R represents a H or methyl group and $R_1$ represents a $C_2$–$C_{12}$ alkylene group or a $C_2$–$C_{12}$ oxyalkylene group containing one or more oxygen atoms joining alkylene segments of the groups, each such segment having a chain length of at least two carbon atoms extending between the oxygen atoms and a level of dicyclopentenyloxy(meth)acrylate in the range of from 0 to 0.2 weight % based on weight of said at least one dicyclopentenyl ester.

2. The composition of claim 1 wherein said level of dicyclopentenyloxy(meth)acrylate is in the range of 0 to 0.1 wt % based on the weight of said at least one dicyclopentenyl ester.

3. The composition of claim 1 wherein $R_1$ is $C_2$–$C_4$ alkylene group.

4. The composition of claim 1 wherein R is a methyl group.

5. The composition of claim 1 further comprising a polymerization inhibitor.

6. The composition of claim 1 further comprising a polymeric binder.

7. The composition of claim 6 wherein the binder is an emulsion polymer.

8. A process for preparing a low odor composition of a dicyclopentenyl ester selected from the group of dicyclopentenyl esters having formula I:

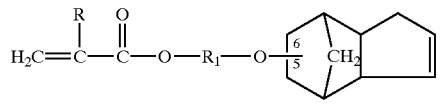

wherein R represents a H or methyl group and $R_1$ represents a $C_2$–$C_{12}$ alkylene group or a $C_2$–$C_{12}$ oxyalkylene group containing one or more oxygen atoms joining alkylene segments of the groups, each such segment having a chain length of at least two carbon atoms extending between the oxygen atoms, comprising the steps of:
a) preparing a distillation mixture comprising:
i) said dicyclopentenyl ester and
ii) from 10 to 10,000 parts per million by weight based on weight of said dicyclopentenyl ester, of at least one inhibitor selected from the group consisting of phenothiazine, 4-hydroxy-2,2,6,6-tetramethyl piperidinyloxy free radical, 4-methacryloyloxy-2,2,6,6-tetramethyl piperidinyloxy free radical, 4-hydroxy-2,2,6,6-tetramethyl N-hydroxy piperidine, cupric acetate, cupric chloride, 2,6-dichlorobenzoquinone, 2-nitrophenol, p-phenylenediamine, and 1,4-naphthoquinone;
b) distilling said distillation mixture at a temperature in the range of 140° C. to 250° C.;
c) collecting at least one first distillation fraction comprising from 2 to 30 weight % of said dicyclopentenyl ester, based on the weight of said dicyclopentenyl ester in said distillation mixture; and
d) collecting at least one second distillation fraction comprising from 98 to 70 weight % of said dicyclopentenyl ester, based on the weight of said dicyclopentenyl ester in said distillation mixture; wherein the level of dicyclopentenyloxy(meth)acrylate in said second distillation fraction is in the range of 0 to 0.2 weight %, based on the weight of said dicyclopentenyl ester in said second distillation fraction, wherein said second distillation fraction is said low odor composition of said dicyclopentenyl ester.

9. The process of claim 8 wherein $R_1$ is $C_2$–$C_4$ alkylene group.

10. The process of claim 8 wherein R is a methyl group.

11. The process of claim 8 wherein said inhibitor is selected from the group consisting of 4-hydroxy-2,2,6,6-tetramethyl piperidinyloxy free radical, 4-methacryloyloxy-2,2,6,6-tetramethyl piperidinyloxy free radical, and 4-hydroxy-2,2,6,6-tetramethyl N-hydroxy piperidine.

12. In a composition comprising:
at least one compound selected from the group of compounds having formula I:

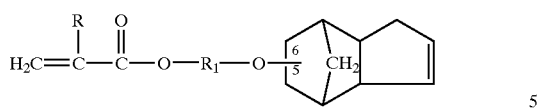

wherein R represents a H or methyl group and $R_1$ represents a $C_2$–$C_{12}$ alkylene group or a $C_2$–$C_{12}$ oxyalkylene group containing one or more oxygen atoms joining alkylene segments of the groups, each such segment having a chain length of at least two carbon atoms extending between the oxygen atoms; wherein the improvement comprises: said composition having a level of dicyclopentenyloxy(meth) acrylate in the range of 0 to 0.2%, based on the weight of said compounds of formula I.

* * * * *